(12) United States Patent  
Vartiainen et al.

(10) Patent No.: US 11,123,234 B2  
(45) Date of Patent: Sep. 21, 2021

(54) ABSORBENT ARTICLE

(71) Applicant: Essity Hygiene and Health Aktiebolag, Gothenburg (SE)

(72) Inventors: Kent Vartiainen, Gothenburg (SE); David Lindqvist, Gothenburg (SE)

(73) Assignee: ESSITY HYGIENE AND HEALTH AKTIEBOLAG, Gothenburg (SE)

(*) Notice: Subject to any disclaimer, the term of this patent is extended or adjusted under 35 U.S.C. 154(b) by 0 days.

(21) Appl. No.: 16/467,752

(22) PCT Filed: Dec. 1, 2017

(86) PCT No.: PCT/SE2017/051201  
§ 371 (c)(1),  
(2) Date: Jun. 7, 2019

(87) PCT Pub. No.: WO2018/117932  
PCT Pub. Date: Jun. 28, 2018

(65) Prior Publication Data  
US 2020/0060887 A1 Feb. 27, 2020

(30) Foreign Application Priority Data  
Dec. 19, 2016 (WO) ................ PCT/SE2016/051283

(51) Int. Cl.  
*A61F 13/472* (2006.01)  
*A61F 13/15* (2006.01)  
(Continued)

(52) U.S. Cl.  
CPC ...... *A61F 13/472* (2013.01); *A61F 13/15747* (2013.01); *A61F 13/55135* (2013.01);  
(Continued)

(58) Field of Classification Search  
CPC ............. A61F 13/15747; A61F 13/551; A61F 13/55135; A61F 13/47; A61F 13/472;  
(Continued)

(56) References Cited

U.S. PATENT DOCUMENTS 5,234,422 A * 8/1993 Sneller ................ A61F 13/4752  
604/385.25  
5,762,642 A * 6/1998 Coles .................. A61F 13/4755  
604/367  
(Continued)

FOREIGN PATENT DOCUMENTS

CN 105555238 A 5/2016  
EP 2130522 A1 12/2009  
(Continued)

OTHER PUBLICATIONS

Australian Examination Report for Australian Application No. 2017379560, dated Sep. 2, 2019, 3 pages.  
(Continued)

*Primary Examiner* — Tatyana Zalukaeva  
*Assistant Examiner* — Heather K Barnwell  
(74) *Attorney, Agent, or Firm* — Buchanan Ingersoll & Rooney P.C.

(57) ABSTRACT

A folded absorbent article with an absorbent core having at least two core layers located between a topsheet and a backsheet is provided. The width of a transition between front and intermediate portions of the core is narrower than a width of the rest of the core. A first end portion of the article is folded about a fold line that coincides with or is adjacent the narrow portion of the core. A second end portion of the article is folded about a second and rear transversal fold line. The first end portion may be folded onto a central area and the second end portion may then be folded onto the first end portion, or the second end portion  
(Continued)

may be folded onto the central area and the first end portion may then be folded onto the second end portion.

24 Claims, 4 Drawing Sheets

(51) Int. Cl.
*A61F 13/551* (2006.01)
*A61F 13/47* (2006.01)
*A61F 13/535* (2006.01)

(52) U.S. Cl.
CPC ..... *A61F 13/535* (2013.01); *A61F 2013/4708* (2013.01); *A61F 2013/5355* (2013.01)

(58) Field of Classification Search
CPC ........ A61F 2013/4708; A61F 14/49001; A61F 14/4704; A61F 14/47; A61F 14/472; A61F 2013/4581; A61F 2013/530437; A61F 2013/530445; A61F 2013/53445; A61F 2013/5355; A61F 12/4707; A61F 12/4704; A61F 12/47; A61F 12/534; A61F 12/53049; A61F 12/5513; A61F 12/55135; A61F 12/5514; A61F 12/535; A61F 13/47218; A61F 13/4704; A61F 13/49001

See application file for complete search history.

(56) References Cited

U.S. PATENT DOCUMENTS

| | | | | |
|---|---|---|---|---|
| 2002/0013562 | A1* | 1/2002 | Mizutani | A61F 13/47263 604/385.01 |
| 2007/0233031 | A1* | 10/2007 | Benson | B65D 83/0805 604/385.02 |
| 2007/0250031 | A1 | 10/2007 | Woltman et al. | |
| 2010/0121296 | A1* | 5/2010 | Noda | A61F 13/532 604/367 |
| 2010/0191205 | A1* | 7/2010 | Carbonari | A61F 13/5514 604/359 |
| 2010/0280479 | A1* | 11/2010 | Svensson | A61F 13/535 604/385.23 |
| 2011/0073513 | A1* | 3/2011 | Weisman | A61F 13/15203 206/494 |
| 2013/0144241 | A1* | 6/2013 | Persson | A61F 13/53713 604/370 |
| 2013/0317470 | A1* | 11/2013 | Kato | A61F 13/5514 604/385.02 |
| 2015/0313769 | A1 | 11/2015 | Dahl et al. | |

FOREIGN PATENT DOCUMENTS

| | | | |
|---|---|---|---|
| EP | 2659866 | A1 | 11/2013 |
| GN | 202682195 | U | 1/2013 |
| GN | 104869964 | A | 8/2015 |
| JP | H08-510664 | A | 11/1996 |
| JP | 2006149413 | A | 6/2006 |
| JP | 2010115403 | A | 5/2010 |
| JP | 2011-130799 | A | 7/2011 |
| JP | 2011130799 | A * | 7/2011 |
| JP | 5215819 | B2 | 6/2013 |
| JP | 2015-500055 | A | 1/2015 |
| WO | 94/27538 | A1 | 12/1994 |
| WO | 2013/081515 | A1 | 6/2013 |
| WO | 2013185800 | A1 | 12/2013 |
| WO | 2013186098 | A1 | 12/2013 |
| WO | 2014196092 | A1 | 12/2014 |
| WO | WO-2015094044 | A1 * | 6/2015 ....... A61F 13/47218 |

OTHER PUBLICATIONS

International Search Report and Written Opinion for International Application No. PCT/SE2017/051201, dated Jan. 30, 2019, 12 pages.
Office Action (Notification of the First Office Action) dated Oct. 24, 2019 by the China National Intellectual Property Administration (CNIPA) of the People's Republic of China in corresponding Chinese Patent Application No. 201780073767.9, and an English Translation of the Office Action. (18 pages).
Office Action (Notification of the Second Office Action) dated May 12, 2020, by the China National Intellectual Property Administration (CNIPA) of the People's Republic of China in corresponding Chinese Patent Application No. 201780073767.9, and an English Translation of the Office Action. (13 pages).
Notice of Reasons for Rejection dated Jun. 15, 2020, by the Japanese Patent Office in corresponding Japanese Patent Application No. 2019-532997 and an English translation of the Office Action. (10 pages).
Extended European Search Report dated Jul. 16, 2020, issued by the European Patent Office in corresponding European Application No. 17882519.6-1102, (7 pages).
Notice of Reasons for Rejection dated Oct. 12, 2020, by the Japanese Patent Office in corresponding Japanese Patent Application No. 2019-532997 and an English translation of the Notice. (7 pages).
Office Action (Decision of Rejection) dated Sep. 2, 2020 by the State Intellectual Property Office of the People's Republic of China in corresponding Chinese Patent Application No. 201780073767.9 and an English Translation of the Office Action. (12 pages).

* cited by examiner

ABSORBENT ARTICLE

CROSS REFERENCE TO RELATED APPLICATIONS

This is a U.S. National Phase application of PCT/SE2017/051201, filed Dec. 1, 2017, which claims priority to PCT/SE2016/051283, filed Dec. 19, 2016, the disclosures of which are incorporated herein by reference in their entireties for all purposes.

TECHNICAL FIELD

The present disclosure concerns an absorbent article such as a sanitary napkin or pad. The present disclosure also concerns methods for folding an absorbent article.

BACKGROUND

Absorbent articles of the kind that is worn inside ordinary underpants include absorbent napkins or pads for adult incontinence or feminine use.

The napkins or pads are generally provided with an absorbent core to receive and retain body liquids. For such absorbent articles to function efficiently, the absorbent core must quickly acquire body liquids into the structure from the point of application and subsequently distribute the body liquids within and throughout the absorbent core to provide maximum leakage containment. The articles should also be comfortable and discrete. WO2013186098A1 discloses an absorbent article for improved fit and leakage protection. It is also desirable that the article should be neat and easily foldable to obtain individual package sizes for easy bring along of the article in a bag or pocket and for easy disposal after use.

SUMMARY

It is an object of the present invention to provide an improved solution that alleviates the mentioned drawback.

The invention concerns a folded absorbent article according to claim 1, a package comprising a plurality of the folded absorbent articles according to claim 16, and methods according to claims 17 and 18 providing new and improved easy folding's of an absorbent article having a new and improved structure.

As such, the present disclosure concerns a folded absorbent article comprising a fluid permeable topsheet, a backsheet and an absorbent core comprising at least two core layers located between the topsheet and the backsheet, a first core layer being located between the topsheet and the second core layer, the topsheet and the backsheet extending together laterally outside the absorbent core, the core in its longitudinal direction having a front portion, a rear portion and an intermediate portion located between the front portion and the rear portion, a transversal width of a transition between the front portion and the intermediate portion of the core being narrower than the transversal width of the rest of the core, a first end portion of the article being folded about a first transversal fold line over a central area of the article, the first fold line coinciding or being adjacent the narrow transversal transition between the front portion and the intermediate portion of the core, the first core layer extends over the intermediate portion and at least a part of the front portion of the absorbent core and the second core layer extending over the front, intermediate and rear portions of the absorbent core, and wherein a second end portion of the article is folded about a second transversal fold line over the central area of the article, the second fold line is adjacent a rear transversal edge of the first core layer, wherein (i) the first end portion is folded onto the central area and the second end portion is folded onto the first end portion or (ii) the second end portion is folded onto the central area and the first end portion is folded onto the second end portion.

The fact that the second fold line is adjacent the rear transversal edge of the first core layer facilitates the folding of the second end portion over the central portion. Additionally, since the second end portion thus essentially only comprises the second core layer the folded absorbent article has a reduced and homogenous thickness. The reduced and homogenous thickness of the folded absorbent articles improves the stackability of the absorbent articles in a package comprising a plurality of the folded absorbent articles. Thus a stable package with a reduced size may be achieved.

The present disclosure also relates to a package comprising a plurality of the folded absorbent articles.

According to one aspect, the present disclosure relates to a method of folding an absorbent article comprising a fluid permeable topsheet, a backsheet and an absorbent core comprising at least two core layers located between the topsheet and the backsheet, a first core layer being located between the topsheet and the second core layer, the topsheet and the backsheet extending together laterally outside the absorbent core, the core in its longitudinal direction having a front portion, a rear portion and an intermediate portion located between the front portion and the rear portion, a transversal width of a transition between the front portion and the intermediate portion of the core being narrower than the transversal width of the rest of the core, comprising:

a) folding a first end portion of the article about a first transversal fold line onto a central area of the article, the first fold line coinciding with or being adjacent the narrow transversal transition between the front portion and the intermediate portion of the core; and b) folding a second end portion of the article about a second transversal fold line onto the first folded end portion, the second fold line being adjacent a rear transversal edge of the first core layer, the first core layer extending over the intermediate portion and at least a part of the front portion of the absorbent core and the second core layer extending over the front, intermediate and rear portions of the absorbent core.

According to a further aspect, the present disclosure relates to a method of folding an absorbent article comprising a fluid permeable topsheet, a backsheet and an absorbent core comprising at least two core layers located between the topsheet and the backsheet, a first core layer being located between the topsheet and the second core layer, the topsheet and the backsheet extending together laterally outside the absorbent core, the core in its longitudinal direction (A) having a front portion, a rear portion and an intermediate portion located between the front portion and the rear portion, a transversal width of a transition between the front portion and the intermediate portion of the core being narrower than the transversal width of the rest of the core, comprising:

a) folding a second end portion of the article about a second transversal fold line onto a central area of the article, b) folding a first end portion of the article about a first transversal fold line onto the second folded end portion, the first fold line coinciding with or being adjacent the narrow transversal transition between the front portion and the intermediate portion of the core; and c) the second fold line being adjacent a rear transversal edge of the first core layer, the first core layer extending over the intermediate portion and at least a part of the front portion of the absorbent core and the second core layer extending over the front, intermediate and rear portions of the absorbent core.

The absorbent article may be in the form of an incontinence pad or a sanitary napkin. The article may be for feminine or incontinence use, and may have an elongate, generally rectangular shape when fully extended in all directions. In this context, a generally rectangular shape is intended to encompass also that, for instance, the corners of the absorbent article may be rounded, or that the edges of the absorbent article may not be completely linear. The absorbent article may have two longitudinal side edges having equal length and extending generally in the same direction.

The topsheet and the backsheet of the absorbent article may extend together laterally outside the absorbent core along the whole circumference of the article and be connected to each other in an edge joint around the periphery of the absorbent core for leakage security. The topsheet may cover part of the backsheet to form an edge barrier.

The topsheet may consist of any material which is suitable for the purpose, i.e. be soft and liquid pervious. Examples of topsheet materials are nonwoven materials, perforated plastic films, plastic or textile mesh, and fluid permeable foam layers. Laminates consisting of two or more topsheet materials may also be employed, as are top sheets consisting of different materials within different parts of the fluid permeable wearer-facing surface.

The backsheet may be fluid impermeable. Backsheet materials that are only fluid repellant may be used particularly in instances where relatively small amounts of urine are expected to be taken up. The backsheet may be a thin, flexible, fluid-impermeable plastic film, such as of polyethylene or polypropylene, but fluid-impermeable nonwoven materials, fluid impermeable foams and fluid impermeable laminates are also contemplated. The backsheet may be breathable, implying that air and vapor may pass through the backsheet.

Furthermore, the backsheet may have an outer, garment-facing surface of a nonwoven material.

The core in its longitudinal direction has a front portion, a rear portion and an intermediate portion located between the front portion and the rear portion, a transversal width of a transition between the front portion and the intermediate portion of the core is narrower than the transversal width of the rest of the core. A transversal width of the transition between the front portion and the intermediate portion of the core may be 50-75% of the widest width of the front portion of the absorbent core.

The absorbent core comprises at least two absorbent core layers. A first core layer is located between the topsheet and the second core layer. The first core layer extends over the intermediate portion and at least a part of the front portion of the absorbent core and the second core layer extends over the front, intermediate and rear portions of the absorbent core. The first core layer may not extend into the rear portion of the absorbent core. The first core layer may have an extension into the front portion of the absorbent core of up to 75%, or up to 60% of the longitudinal length of the front portion of the absorbent core. The front portion, the rear portion and the intermediate portion of the core may be of substantially equal length. The length of each of the front portion, the rear portion and the intermediate portion of the core may each constitute 25-40% of the longitudinal length of the absorbent core. The front portion of the second absorbent layer may constitute 20-40% of the total longitudinal length of the second absorbent layer. The surface area of the first core layer may be 30-60% of the surface area of the second core layer.

The thickness of the rear portion of the absorbent core may be 25-70% of the thickness of the intermediate portion of the core, or may be 30-60%, or 35-50%, facilitating an easy fold. The thickness of the front portion of the absorbent core may be 25-70% of the thickness of the intermediate portion of the core, or may be 30-60%, or 35-50% facilitating an easy fold.

The absorbent core may be made up of any suitable absorbent or fluid uptake material, such as one or more layers of cellulose fluff pulp, foam, highloft, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. The absorbent structure may comprise at least 20% superabsorbents and may comprise 20-80% superabsorbents and 80-20% pulp fibres. The absorbent core may further incorporate components for improving the properties of the absorbent core. Some examples of such components are binder fibers, fluid-dispersing materials, wetness indicators, fluid acquisition materials, etc.

The absorbent layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibres and superabsorbent material, wherein the ratio of superabsorbent material to fibres may vary in the layer.

An acquisition layer may be located between the topsheet and the absorbent core. The acquisition layer may be of a rectangular shape. The acquisition layer may have a surface extension covering the surface area of the longitudinal extension of the first core layer. The acquisition layer may be surrounded in the longitudinal and lateral directions by portions of the absorbent core. The acquisition layer may not extend into the rear portion of the absorbent core and thereby facilitating a fold about the second fold line. The acquisition layer may have an extension in the longitudinal direction beyond the rear transversal fold line and thus beyond the extension of the first core layer, such an arrangement has the advantage of providing resilience to the folding about the second fold line and providing improved fluid transport across the fold line to the rear part of the absorbent core.

An elastic member may be arranged along each longitudinal side edge of the article, at least laterally outside of the transition between the front portion and the intermediate portion of the core. The elastic members may be located between the topsheet and the backsheet. The article may have an interspace free from absorbent material located between the elastic member and the transition between the front portion and the intermediate portion of the core, more specifically in an area between the elastics, located at the periphery of the article, and the periphery of the first absorbent layer. Each elastic member may have an extension at least to a lateral edge of a widest part of the front portion of the absorbent core to facilitate the fold of the first end portion of the article. The elastic member may not extend in the longitudinal direction beyond the rear transversal edge of the rear part of the first core layer to facilitate the fold. The elastic members may not extend beyond the second fold line of the article to facilitate fold about the fold line.

The absorbent article may further include fastening means for fastening of the absorbent article inside a supporting pant garment, such as a pair of underpants. The fastening means may be covered by a releasable protective layer.

The absorbent article comprises at least twofold lines. A fold line may or may not be visible on the absorbent article. A fold line is a location of the article wherein folding is facilitated due to the construction of the article. The first transversal fold line of the article is coinciding with or adjacent the narrow transversal transition between the front portion and the intermediate portion of the core. The folding about this first fold line is facilitated by the narrow transversal transition between the two core portions having a narrower width than the rest of the core. The second fold line is adjacent the rear transversal edge of the first core layer, thus just beyond the longitudinal extension of the first core layer. Adjacent as defined herein is a feature lying close or nearby another feature. The first core layer has a shorter longitudinal extension than the second core layer and is the core layer being closest to the topsheet. The folding about the second fold line is facilitated by the relative sizes of the first and second core layers and their relative positions providing less stiffness and less resistance to folding compared with other core constructions. The folding about the first and second fold lines may be further facilitated by the location of possible elastic members, acquisition layer, relative thickness of the absorbent core etc., as disclosed herein.

The first end portion of the article comprises the front portion of the core. A central area of the article comprises the intermediate portion of the core. The second end portion of the article comprises the rear portion of the core.

According to one aspect of the present invention, the first fold is accomplished by folding the first end portion of the article about a first transversal fold line onto a central area of the article, the first fold line coinciding or being adjacent the narrow transversal transition between the front portion and the intermediate portion of the core. The result of the first fold is that the topsheet of the first end portion of the article is facing the topsheet of the central area of the article. The second fold is accomplished by folding the second end portion of the article about a second transversal fold line onto the first folded end portion, the second fold line being adjacent a rear transversal edge of the first absorbent core layer. The result of the second fold is that the topsheet of the second end portion of the article is facing the backsheet of the first folded end portion of the article.

According to another aspect of the present disclosure, the first fold is accomplished by folding the second end portion of the article about the second transversal fold line onto the central area of the article, the second fold line being adjacent a rear transversal edge of the first absorbent core layer. The second fold is accomplished by folding the first end portion of the article about the first transversal fold line onto the second folded end portion, the first fold line coinciding or being adjacent the narrow transversal transition between the front portion and the intermediate portion of the core. The result of the first fold is that the topsheet of the second end portion of the article is facing the topsheet of the central area of the article. The result of the second fold is that the topsheet of the first end portion of the article is facing the backsheet of the second folded end portion of the article. It should be noted that there is no difference if the second end portion and the second fold line is the subject of the first folding step and the first end portion and the first fold line the subject of the second folding step.

BRIEF DESCRIPTION OF THE DRAWINGS

The invention will be more closely described with reference to the enclosed Figures, in which.

DETAILED DESCRIPTION OF PARTICULAR EMBODIMENTS

Figure 1:
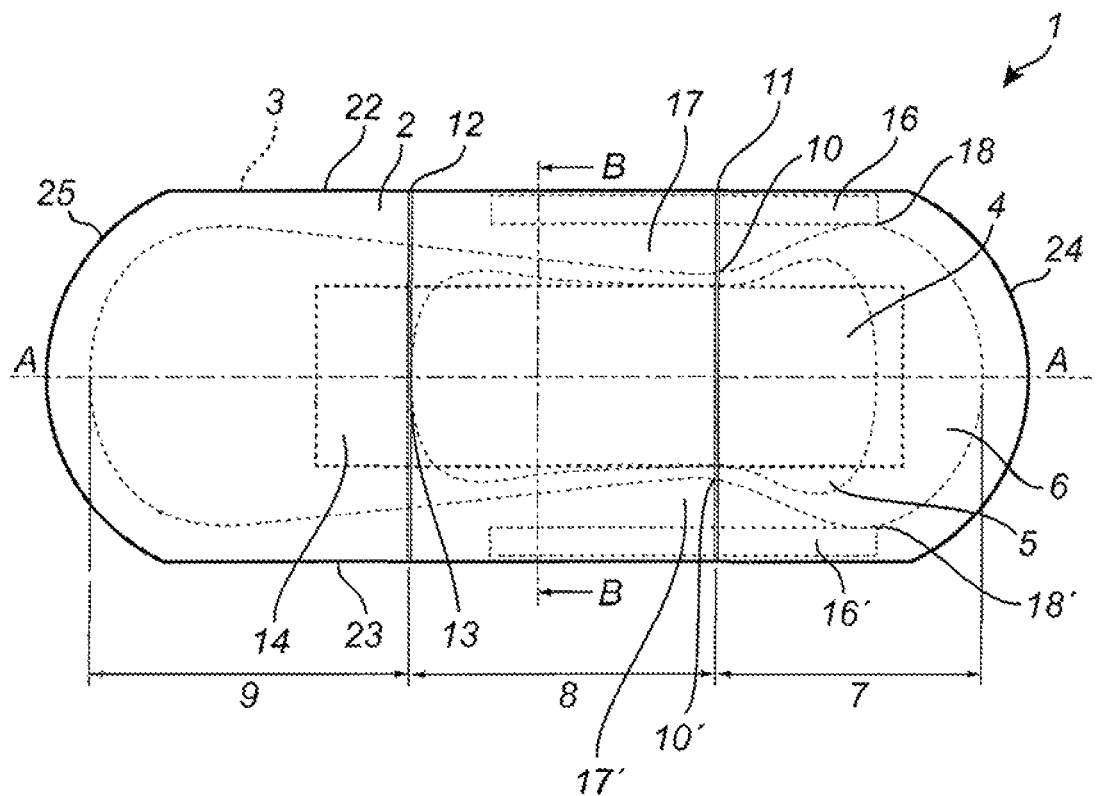
FIG. 1 is a top plan view of an exemplary absorbent article of the invention.
Figure 2:
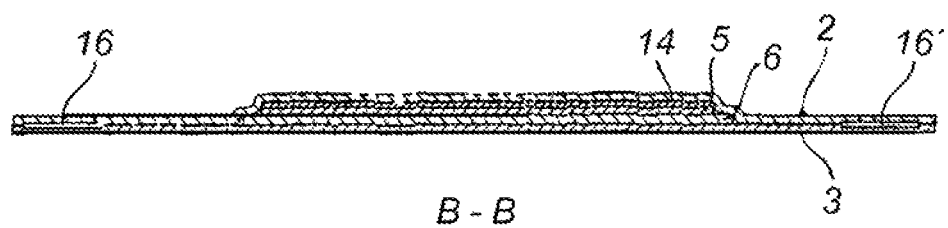
FIG. 2 is a cross-sectional view along the line B-B of the absorbent article of FIG. 1.

The invention will be described more closely below by an exemplary embodiment. The invention may however be embodied in many different forms and should not be construed as limited to the embodiments set forth in the drawings and the description thereto.

FIG. 1 schematically shows an absorbent article 1 in the form of an incontinence pad seen from the side that is intended to be facing towards a wearer's body when the article 1 is being worn. The article 1 has two longitudinal side edges 22, 23 having equal length and extending generally in the same direction. Front and rear end edges 24, 25 extend transversely at the ends of the article 1. The rear end edge 25 is intended to be oriented rearwards during use of the article 1, and the front-end edge 24 is intended to be facing forwards towards the abdomen of the wearer. The article 1 comprises a fluid permeable topsheet 2, a fluid impermeable backsheet 3 and an absorbent core 4 comprising at least two core layers 5, 6. A first core layer 5 is located between the topsheet 2 and the second core layer 6. The second core layer 6 is located between the first core layer 5 and the backsheet 3. The core 4 has in its longitudinal direction a front portion 7, a rear portion 9 and an intermediate portion 8 located between the front portion 7 and the rear portion 9. The first core layer 5 extends over the intermediate portion 8 and at least a part of the front portion 7 of the absorbent core 4. The second core layer 6 extends over the front 7, intermediate 8 and rear portion 9 of the absorbent core. The absorbent core 3 has a narrow transversal width 10-10' between the front portion 7 and the intermediate portion 8 of the core 3. The absorbent core comprises a mixture of superabsorbent particles and pulp fibers.

The article has an acquisition layer 14 located between the topsheet 2 and the absorbent core 4. The acquisition layer has an extension over the intermediate portion 8 of the absorbent core 4 and partly extending into the front 7 and rear 9 portions of the core 4.

The topsheet 2 and the backsheet 3 extends together laterally outside the absorbent core 4 along the whole circumference and are connected to each other in an edge join around the periphery of the article 1. The edge join may be formed in any suitable manner as known in the art such as by adhesive, ultrasonic bonding, thermo-bonding etc. The topsheet 2 and the backsheet 3 may consist of any material suitable, such as nonwoven or film material, for the purpose as disclosed herein.

Elastic members 16, 16', such as band of elastic material, e.g. foam elastics, are arranged between the topsheet 2 and the backsheet 3 and along the longitudinal side edges 22, 23 of the article 1. The article has an interspace 17, 17' free from absorbent material located laterally between the elastic member 16, 16' and the transition between the front portion 7 and the intermediate portion 8 of the core 4. Each elastic member extends to a lateral edge 18, 18' of the widest part of the front portion 7 of the absorbent core 4.

An example of an article of the present disclosure is the incontinence pad of FIG. 1 having a topsheet of 18 gsm spunbonded thermoplastic nonwoven material, an acquisition layer of a 50 gsm nonwoven highloft of PP and PET. The core is of 35% SAP and 65% pulp fibers. The backsheet is a 25 gsm laminate of a plastic film and a thermoplastic nonwoven material. The components of the article are connected to each other by means of adhesive and welding.

Figure 3A:
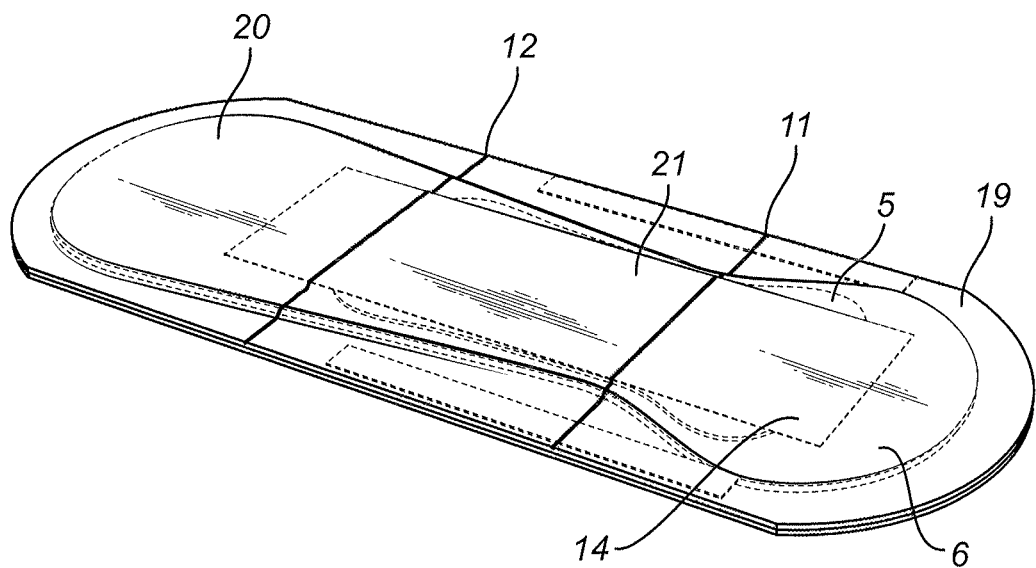
FIGS. 3a-3d are elevation views of successive steps of folding the absorbent article of FIG. 1.
Figure 3B:
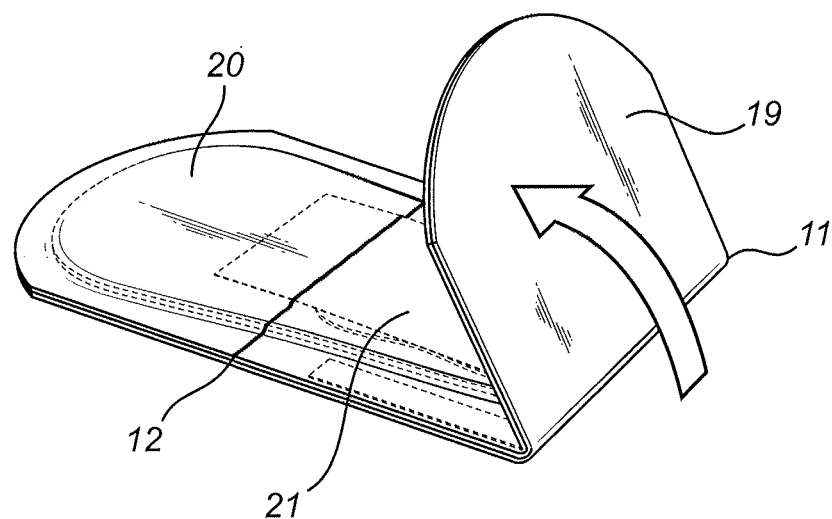
Figure 3C:
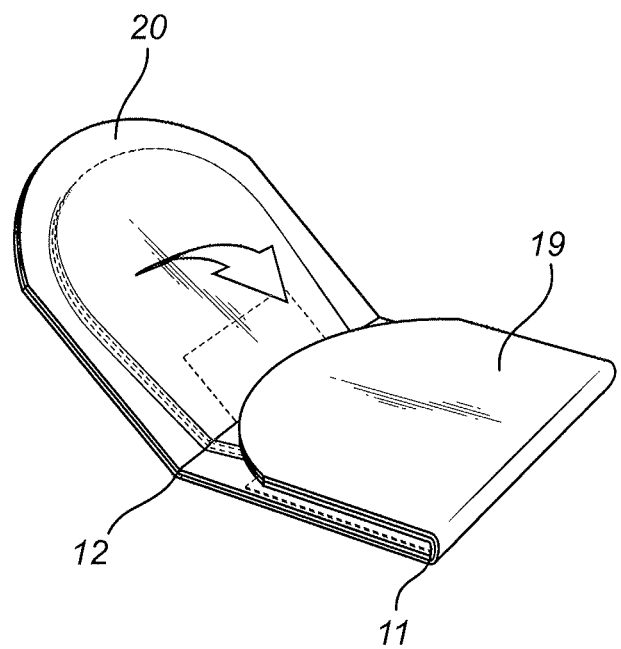
Figure 3D:
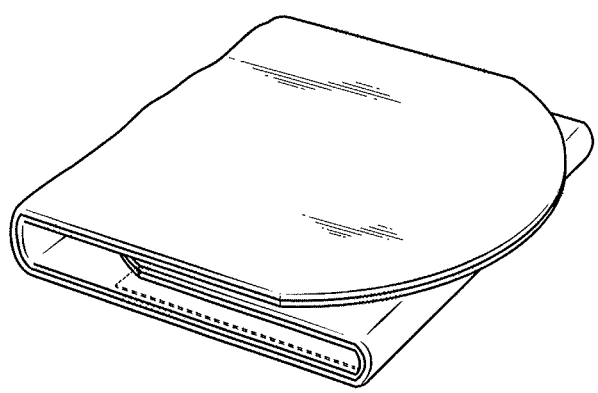

FIGS. 3a to 3d illustrate the two folding steps of the absorbent article. Starting from FIG. 3a showing the unfolded article 1 and the first 11 and second 12 folding lines, the first end portion 19, the second end portion 20 and the central area 21 of the article. In FIG. 3b the first end portion 19 of the article 1 is folded about the first transversal fold line 11 coinciding with or being adjacent the narrow transversal transition between the front portion 7 and the intermediate portion 8 of the core 4 until the first end portion 19 is in contact with the central area 21 of the article 1, i.e. folding until topsheet 2 of the first end portion 19 is in contact with the topsheet 2 of the central area 21. In FIG. 3c a second end portion 20 of the article 1 is folded about the second transversal fold line 12 adjacent a rear transversal edge 13 of the first absorbent core layer 5 until it is in contact with the portion 19 of the article 1 already folded, i.e. the topsheet 2 of second end portion 20 facing the backsheet 3 of the first end portion 19. FIG. 3d shows the final folded article 1.

Figure 4A:
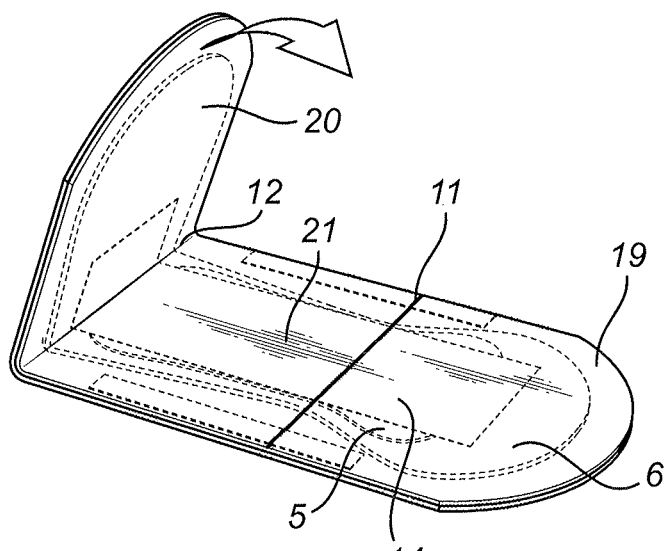
FIGS. 4a-4c are elevation views of successive steps of an alternative folding the absorbent article of FIG. 1.
Figure 4B:
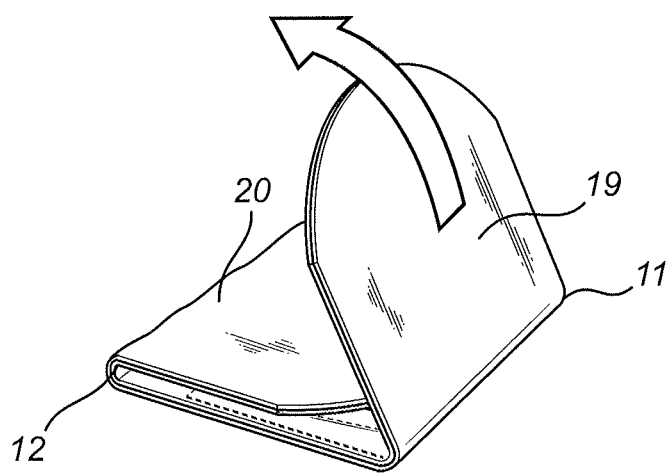
Figure 4C:
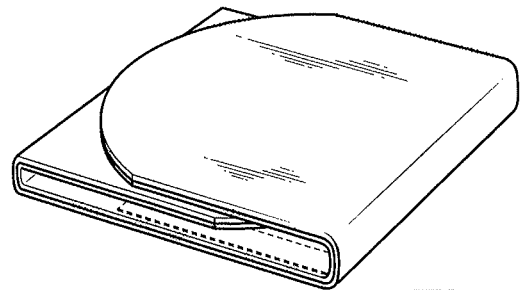

FIGS. 4a to 4c illustrate the two folding steps of the absorbent article shown in FIG. 3a. In FIG. 4a a second end portion 20 of the article 1 is folded in a first folding step about the second transversal fold line 12 adjacent the rear transversal edge 13 of the first core layer 5 until the second end portion 20 is in contact with the central area 21 of the article 1, i.e. folding until topsheet 2 of the second end portion 20 is in contact with the topsheet 2 of the central area 21. FIG. 4b illustrates the second folding step, wherein a first end portion 19 of the article 1 is folded about the first transversal fold line 11 coinciding with or being adjacent the narrow transversal transition between the front portion 7 and the intermediate portion 8 of the core 4 until it is in contact with the portion 19 of the article 1 already folded, i.e. the topsheet 2 of first end portion 19 facing the backsheet 3 of the second end portion 20. FIG. 4c shows the final folded article 1.

The invention claimed is:

1. A folded absorbent article comprising a fluid permeable topsheet, a backsheet and an absorbent core, the absorbent core comprising at least a first core layer and a second core layer, the first and second core layers being located between the topsheet and the backsheet, the first core layer being located between the topsheet and the second core layer, the topsheet and the backsheet extending together laterally outside the absorbent core, the absorbent core in its longitudinal direction having a front portion, a rear portion and an intermediate portion located between the front portion and the rear portion, a transversal width of a transversal transition between the front portion of the absorbent core and the intermediate portion of the absorbent core being narrower than a transversal width of a rest of the absorbent core, a first end portion of the article being folded about a first transversal fold line over a central area of the article, the first fold line coinciding with or being adjacent to the transversal transition between the front portion of the absorbent core and the intermediate portion of the absorbent core, the first core layer being folded about the first fold line;

wherein the first core layer extends over the intermediate portion of the absorbent core and at least a part of the front portion of the absorbent core, and the second core layer extends over the front, intermediate and rear portions of the absorbent core, and wherein a second end portion of the article is folded about a second transversal fold line over the central area of the article, the second transversal fold line being adjacent to a rear transversal edge of the first core layer such that the first core layer does not extend beyond the second transversal fold line, and wherein (i) the first end portion of the article is folded onto the central area of the article and the second end portion of the article is folded onto the first end portion of the article, or (ii) the second end portion of the article is folded onto the central area of the article and the first end portion of the article is folded onto the second end portion of the article; and wherein the absorbent article is free of any core layer between the topsheet and the second core layer at the second transversal fold line.

2. The absorbent article according to claim 1, wherein the article is a sanitary napkin or pad.

3. The absorbent article according to claim 1, wherein the first core layer does not extend into the rear portion of the absorbent core.

4. The absorbent article according to claim 1, wherein the front portion, the rear portion and the intermediate portion of the absorbent core are of substantially equal length.

5. The absorbent article according to claim 1, wherein a front portion of the second core layer constitutes 20-40% of a total longitudinal length of the second core layer.

6. The absorbent article according to claim 1, wherein a thickness of the rear portion of the absorbent core is 25-70% of a thickness of the intermediate portion of the absorbent core.

7. The absorbent article according to claim 1, wherein a thickness of the front portion of the absorbent core is 25-70% of a thickness of the intermediate portion of the absorbent core.

8. The absorbent article according to claim 1, wherein the article further comprises an acquisition layer located between the topsheet and the absorbent core and wherein the acquisition layer comprises a surface extension covering at least a surface area of a longitudinal extension of the first core layer.

9. The absorbent article according to claim 8, wherein the acquisition layer has an extension in the longitudinal direction beyond the second transversal fold line and extends into the rear portion of the absorbent core.

10. The absorbent article according to claim 1, wherein the transversal width of the transversal transition between the front portion of the absorbent core and the intermediate portion of the absorbent core is 50-75% of a widest width of the front portion of the absorbent core.

11. The absorbent article according to claim 1, wherein at least one elastic member is arranged along a respective longitudinal side edge of the article, and each of the at least one elastic member is arranged at least laterally outside of the transversal transition between the front portion of the absorbent core and the intermediate portion of the absorbent core.

12. The absorbent article according to claim 11, wherein the article further comprises an at least one interspace located between each of the at least one elastic member and the transversal transition between the front portion of the absorbent core and the intermediate portion of the absorbent core, wherein the at least one interspace is free from absorbent material located between each elastic member and the transversal transition between the front portion of the absorbent core and the intermediate portion of the absorbent core.

13. The absorbent article according to claim 11, wherein each of the at least one elastic member extends in the longitudinal direction at least to a respective lateral edge of a widest part of the front portion of the absorbent core.

14. The absorbent article according to claim 11, wherein each elastic member does not extend in the longitudinal direction beyond the rear transversal edge of the rear part of the first core layer.

15. The absorbent article according to claim 1, wherein a surface area of the first core layer is 30-60% of a surface area of the second core layer.

16. The absorbent article according to claim 1, wherein a central portion of the rear transversal edge of the first core layer protrudes outwardly from lateral-most ends of the rear transversal edge.

17. The absorbent article according to claim 1, wherein the rear portion of the absorbent core is free of any core layer between the topsheet and the second core layer.

18. A package comprising a plurality of the folded absorbent articles according to claim 1.

19. A method of folding an absorbent article, the article comprising a fluid permeable topsheet, a backsheet and an absorbent core comprising at least a first core layer and a second core layer located between the topsheet and the backsheet, the first core layer being located between the topsheet and the second core layer, the topsheet and the backsheet extending together laterally outside the absorbent core, the absorbent core in its longitudinal direction having a front portion, a rear portion and an intermediate portion located between the front portion and the rear portion, a transversal width of a transversal transition between the front portion of the absorbent core and the intermediate portion of the absorbent core being narrower than a transversal width of a rest of the absorbent core, the method comprising:
 a) folding a first end portion of the article about a first transversal fold line onto a central area of the article, the first fold line coinciding with or being adjacent the narrow transversal transition between the front portion of the absorbent core and the intermediate portion of the absorbent core, thereby forming a folded first end portion, the first core layer being folded about the first fold line; and
 b) folding a second end portion of the article about a second transversal fold line onto the folded first end portion, the second fold line being adjacent a rear transversal edge of the first core layer such that the first core layer does not extend beyond the second fold line, the first core layer extending over the intermediate portion of the absorbent core and at least a part of the front portion of the absorbent core and the second core layer extending over the front, intermediate and rear portions of the absorbent core,
 wherein the absorbent article is free of any core layer between the topsheet and the second core layer at the second fold line.

20. The method of folding an absorbent article according to claim 19, wherein a central portion of the rear transversal edge of the first core layer protrudes outwardly from lateral-most ends of the rear transversal edge.

21. The method of folding an absorbent article according to claim 19, wherein the rear portion of the absorbent core is free of any core layer between the topsheet and the second core layer.

22. A method of folding an absorbent article, the article comprising a fluid permeable topsheet, a backsheet and an absorbent core, the absorbent core comprising at least a first core layer and a second core layer located between the topsheet and the backsheet, the first core layer being located between the topsheet and the second core layer, the topsheet and the backsheet extending together laterally outside the absorbent core, the absorbent core in its longitudinal direction having a front portion, a rear portion and an intermediate portion located between the front portion and the rear portion, a transversal width of a transversal transition between the front portion of the absorbent core and the intermediate portion of the absorbent core being narrower than a transversal width of a rest of the absorbent core, the method comprising:
 a) folding a first end portion of the article about a first transversal fold line onto a central area of the article, thereby forming a folded first end portion; and
 b) folding a second end portion of the article about a second transversal fold line onto the folded first end portion, the second fold line coinciding with or being adjacent to the transversal transition between the front portion of the absorbent core and the intermediate portion of the absorbent core, the first core layer being folded about the second fold line,
 wherein the first fold line is adjacent to a rear transversal edge of the first core layer such that the first core layer does not extend beyond the first fold line, the first core layer extending over the intermediate portion and at least a part of the front portion of the absorbent core and the second core layer extending over the front, intermediate and rear portions of the absorbent core, and
 wherein the absorbent article is free of any core layer between the topsheet and the second core layer at the first fold line.

23. The method of folding an absorbent article according to claim 22, wherein a central portion of the rear transversal edge of the first core layer protrudes outwardly from lateral-most ends of the rear transversal edge.

24. The method of folding an absorbent article according to claim 22, wherein the rear portion of the absorbent core is free of any core layer between the topsheet and the second core layer.

* * * * *